United States Patent [19]

Kräemer et al.

[11] 4,070,348

[45] Jan. 24, 1978

[54] WATER-SWELLABLE, BEAD COPOLYMER

[75] Inventors: Dieter Kräemer, Mainz; Klaus Lehmann, Rossdorf via Darmstadt; Horst Pennewiss, Darmstadt-Neu-Kranichstein; Hermann Plainer, Darmstadt; Roland Schweder, Darmstadt-Eberstadt, all of Germany

[73] Assignee: Rohm GmbH, Darmstadt, Germany

[21] Appl. No.: 544,830

[22] Filed: Jan. 28, 1975

Related U.S. Application Data

[63] Continuation-in-part of Ser. No. 382,379, July 25, 1973, abandoned.

[51] Int. Cl.² .............. C08F 28/00; C08G 75/00; C08F 24/00; C08F 2/00
[52] U.S. Cl. .............. 260/79.3 MU; 526/261; 526/264; 526/273; 526/303; 526/320; 526/909; 526/910; 528/493; 195/63; 195/DIG. 11; 260/2.5 R; 260/2.5 B; 260/8; 260/17.45 G; 260/17.4 GC; 260/29.6 TA; 260/29.6 WQ; 260/32.6 N; 260/32.6 NA; 260/32.8 R; 260/78 UA; 260/79.3 M; 424/81; 526/203; 526/219; 526/220; 526/232; 526/260
[58] Field of Search .......... 260/8, 29.6 TA, 29.6 WQ, 260/79.3 M, 79.3 MU, 80.72; 195/63, DIG. 11; 526/909, 910, 273

[56] References Cited

U.S. PATENT DOCUMENTS

| | | | |
|---|---|---|---|
| 2,982,749 | 5/1961 | Friedrich et al. | 260/29.6 WQ |
| 3,317,453 | 5/1967 | MacDonald et al. | 260/80.72 |
| 3,532,679 | 10/1970 | Steckler | 260/80.72 |
| 3,563,953 | 2/1971 | Lehmann et al. | 260/80.72 |
| 3,625,827 | 12/1971 | Wildi et al. | 195/DIG. 11 |
| 3,764,477 | 10/1973 | Lehmann et al. | 195/63 |
| 3,775,253 | 11/1973 | Dieter et al. | 260/8 |
| 3,787,380 | 1/1974 | Stamberger | 260/80.72 |
| 3,806,417 | 4/1974 | Beaucamp | 195/DIG. 11 |
| 3,844,892 | 10/1974 | Matthews | 195/DIG. 11 |
| 3,845,010 | 10/1974 | Labana et al. | 526/273 |
| 3,871,964 | 3/1975 | Hüper et al. | 195/63 |

FOREIGN PATENT DOCUMENTS 1,908,290  9/1970  Germany.

*Primary Examiner*—Herbert J. Lilling
*Attorney, Agent, or Firm*—Curtis, Morris & Safford

[57] ABSTRACT

Water-swellable, cross-linked, bead copolymers of (A) an ethylenically unsaturated monomer having a carboxylic acid anhydride, glycidyl or succinimide group, (B) a comonomer having at least two radical-polymerizable carbon double bonds, and (C) a radical-polymerizable water-soluble comonomer are disclosed to be excellent carriers capable of bonding with biologically active substances such as enzymes, enzyme substrates, inhibitors, hormones, antibiotics, antigens, and peptides.

12 Claims, No Drawings

WATER-SWELLABLE, BEAD COPOLYMER

The present application is a continuation-in-part of copending application Ser. No. 382,379 filed July 25, 1973, now abandoned.

The present invention relates to bead-shaped copolymers which swell in water and, without prior activation attach, by development of a covalent bond, biologically active substances such as enzymes, enzyme substrates, inhibitors, hormones, antibiotics, antibodies, antigens, and peptides which have at least one free primary amino or hydroxyl group. The biologically active substances bound to the bead-shaped polymer thereby retain their specific activities and can be used for corresponding biochemical reactions. The advantages which result from the use of carrier-bound, biologically active substances are generally known — possibility of reuse, greater stability, rapid interruption of the reaction by filtration, absence of contamination of the reaction products, and continuous reactions in columns or similar reactors.

A large number of carrier materials for biologically active substances are known. Although some of them can also be made in the form of well-defined particles, the above-indicated advantages have, however, not been fully achieved by the products known up to the present time.

Carriers having a base of polysaccharides such as cellulose, starch, dextran, agarose and their derivatives can be attacked enzymatically, either by microbiological attack or the presence of hydrolytic enzymes. The "bleeding" of the biologically active substances which is frequently observed in the case of these carriers can be ascribed both to such degradation and to incomplete bonding. For the surface bonding of biologically active substances to inorganic or synthetic materials of defined, compact shape such as glass beads or synthetic fibers, a special activation is necessary. The bonding capacity is very small due to the relatively small surface accessible.

Enzymes embedded in bead form in plastic which, when used as column packing, permit a high speed of flow can be obtained in accordance with a method suggested by Nilsson and Mosbach by polymerizing unsaturated monomers in an aqueous, enzymatic solution with cross-linking. The resultant water-containing polymer beads enclose the enzyme without chemically bonding it. With this method, one can only use dilute enzyme solutions and thus bind only about 3% of active protein. Greater loading of the carrier with active material is not obtainable with more concentrated enzyme solutions, since the active material is damaged by the radical polymerization reaction. Upon use, enzymes can constantly bleed out of the finished product due to swelling and shrinking. On the other hand, if the cross-linking is so great that the enzyme remains completely enclosed, then high-molecular weight substrates can no longer migrate into the beads and react with the enzyme. The same is true of all methods in which biologically active substances are embedded in membranes, sheets, or other semi-permeable layers.

Bead polymers which combine chemically with biologically active substances from aqueous solution are known from DOS(German Published Application for Patent) No. 2,062,818. They are produced by dissolving a solution of maleic anhydride, vinyl ethers and divinyl ethers in a strongly polar solvent, emulsifying the solution in a hydrocarbon so as to form drops and polymerizing it. There are produced swollen polymer beads of wide-meshed cross-linking which are originally relatively hydrophobic. Their hydrophilic nature and thus also their swellability by water increases only upon hydrolysis of the anhydride groups to carboxyl groups. To the extent that hydrolysis and swelling proceed from the outside towards the inside upon contact with an aqueous phase, a biologically active substance dissolved in the aqueous phase can also diffuse into the beads and be bound by the anhydride groups which still remain after extensive hydrolysis.

The hydrophobic nature of the starting materials interferes with the bead polymerization process. The monomers are soluble also in the hydrocarbon phase and polymerize there to a considerable extent, forming a finely divided precipitation polymer which can be separated only with difficulty from the true polymer bead. The precipitation polymer eliminates some of the advantages which reside in the bead shape of the enzyme carrier; it impedes the filterability, does not permit complete separation from a substrate solution, and reduces the speed of flow in column reactors.

One fundamental disadvantage of the polymers resides in the lack of hydrophilic nature in the initial stage. The inward diffusion and combining of the biologically active substances must always precede the hydrolysis and hydrophilization. The anhydride groups are therefore generally completely hydrolyzed before biologically active molecules, and particularly high-molecular substances, can penetrate into the swollen region. The bonding capacity of these enzyme carriers is therefore relatively limited, as is the specific activity, i.e. the proportion of the chemically bound material which has retained its biological activity.

The improved carriers of the present invention have a well-defined head shape and are not accompanied by fine precipitation polymer. They are not enzymatically degradable and are able to bond, with covalent bonds, biologically active substances in high yield and with retention of their biological activity. Such carriers with enzymes bonded thereto are capable of being separated easily and completely from substrate solutions and permit a high speed of flow through a column filled with them. The prerequisite for this is a high free volume between the individual particles in a pile of the particles.

Spherical particles of substantially uniform size satisfy the requirement, but it was not possible up to now to produce carrier substances capable of bonding with enzymes and other biologically active substances in the form of a uniform bead polymer.

The carrier substance of the present invention is a bead-shaped, cross-linked, water-swellable copolymer which is formed of a mixture of the following comonomers:

A. a radical-polymerizable compound which has a group that is capable of reacting with primary amino groups or hydroxyl groups of biologically active substances with the formation of a convalent bond, e.g., a compound having at least one $\alpha,\beta$-ethylenic unsaturation and also a carboxylic acid anhydride group or a glycidyl group, or a compound of the formula

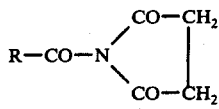

in which R is a hydrocarbon radical containing an α,β-ethylenically unsaturated group, preferably $CH_2=CH-$ or $CH_2=C(CH_3)-$;

B. a cross-linking compound having at least two radical-polymerizable α,β-carbon double bonds, but otherwise free of the functional groups found in monomer A;

C. one or more radical-polymerizable monounsaturated water-soluble compounds, preferably containing a vinyl or vinylidene group and an amido, hydroxy, carboxylic acid, carboxylate, secondary or tertiary amino, quaternary ammonium or sulfonic acid group; and optionally D. other water-insoluble radical-polymerizable monounsaturated compounds.

Comonomers A, B and C constitute 50 to 100 mol percent. Comonomer A is present to the extent of at least 2 mol percent, comonomer B is present to the extent of 0.2 to 5 mol percent, and comonomer C is present to the extent of at least 10 mol percent, referred in each case to the total monomer mixture.

Because of the content of water-soluble comonomers, the monomer mixture used for the bead polymerization is as a whole more hydrophilic and more sharply delimited from the surrounding hydrophobic medium than is true in the production of bead polymers by the method of DOS No. 2,062,818. Uniform polymer beads without accompanying precipitation polymer are produced. Due to their hydrophilic nature, the bead polymers of the invention swell rapidly and extensively in water, so that biologically active substances dissolved in swelling water can also penetrate simultaneously and be bonded by a covalent bond. By way of example, the superiority of the bead polymers of the invention for carrying trypsin as compared with bead polymers obtained in accordance with DOS No. 2,062,818 is demonstrated in the following table.

groups, respectively. Since water is always present in considerable excess with respect to the hydroxyl and amino groups, groups which react spontaneously with water, such as, for instance, isocyanate groups, are less suitable. There are preferably present activated carboxyl groups such as known from peptide chemistry or N- or O-alkylating agents such as alkyl halide or epoxide groups. Examples of activated carboxyl groups which are used in peptide chemistry for the formation of peptide bonds are carbonyl chloride, carboxylic anhydride and carboxylic acid azide groups, as well as phenyl esters and the carboxylates of hydroxylamino derivatives of the formula

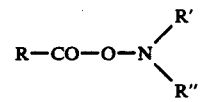

in which R is an α,β-unsaturated, polymerizable radical and R' and R" are identical or different alkyl or alkanoyl groups. R' and R" together with the N atom may also form a heterocyclic ring. Typical compounds of this type are:

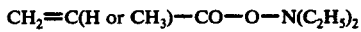

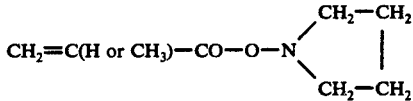

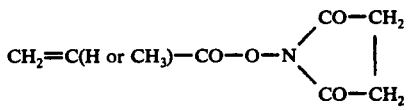

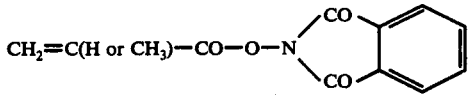

Other compounds having activated carboxyl groups

|  | Carrier | | |
| --- | --- | --- | --- |
|  | DOS 2,062,818 Example 3 | DOS 2,062,818 Example 4 | Application Example 1 |
|  | Butanediol-divinylether/ maleic anhydride (1:2 mol) | Butanediol-divinylether/ ethyl-vinyl-ether/maleic anhydride (1:1:1 mol) | Acrylamide-methacrylic anhydride (1:1 by wt) |
| Relative proportions, dry carrier: trypsin | 2:1 | 2:1 | 3:1 |
| Degree of swelling (0.05 M phosphate buffer-pH 7.5) | 3 | 30 | 28 |
| Trypsin content (dry weight, %) | 0.74 | 1.9 | 22 |
| Yield of bound and penetrated enzyme, % | 15[1] | 3[1] | 89 |
| Mean activity[2] (mU/mg resin) | 1.9 | 1.5 | 41 |
| Stability of the enzymatic activity after repeated use | no | no | yes |

[1]These values were ascertained after several washings without achieving a constant final activity value. The values for covalent-bound protein may be lower.
[2]One mU corresponds to a cleavage of $1 \times 10^{-3}$ μmol peptide bonds per minute as mean value for a reaction time of 60 minutes, measured by automatic titration.

The active groups of comonomer A are groups which react at temperatures of 0° to 40° C. in aqueous solution with primary amino groups and hydroxyl groups and thereby form covalent bonds with the oxygen or hydrogen atoms of the hydroxyl or amino include, by way of example, acrylyl- and methacrylyl chloride, acrylic- and methacrylic anhydride, maleic anhydride, phenyl acrylate and methacrylate, glycidyl acrylate and methacrylate, 4-iodobutyl acrylate and methacrylate and 2-isopropenyl-4,4-dimethyl-oxazolone-5. The last-mentioned compound reacts, for instance, with the terminal amino group of a protein in accordance with the reaction:

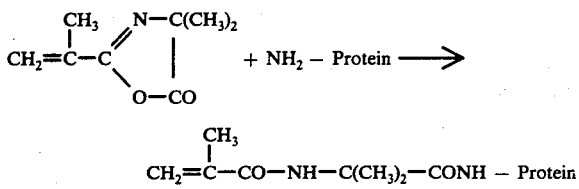

Typical representatives of the N- and O-alkylating comonomers are acrylic- and methacrylic anhydrides, acryloyl-methacryloyl N-hydroxy succinimides, ω-iodo-alkyl esters of acrylic or methacrylic acid in which the alkyl group in general contains two to six carbon atoms, allyl chloride, chlormethyl styrene, chloracetoxy ethyl methacrylate, and compounds having a glycidyl group. The latter are ethers or esters formed between a glycidyl alcohol and an unsaturated alcohol or unsaturated carboxylic acid respectively. The glycidyl alcohols are aliphatic and cycloaliphatic alcohols and ether alcohols having from 3 to 18 carbon atoms which are esterified with an $\alpha,\beta$-unsaturated carboxylic acid, preferably acrylic or methacrylic acid, or are etherified with an olefinically or acetylenically unsaturated alcohol. Typical compounds are glycidyl acrylate and methacrylate; 4,5-epoxy-pentylacrylate; 4-(2,3-epoxypropyl)-n-butyl-methacrylate; 9,10-epoxystearylacrylate; 4-(2,3-epoxypropyl)-cyclohexyl methacrylate; ethylene glycol-monoglycidyl ether-acrylate; and allyl glycidyl ether.

Upon reaction with enzymes, enzyme substrates, inhibitors, hormones, antibiotics, antibodies, antigens and peptides, the said groups form convalent bonds to O- or N-atoms in aqueous solution at temperatures within the range of 0° to 40° C. If the biologically active substances have a protein character, they have a terminal primary amino group as well as in many instances further OH or NH groups in amino acid radicals of ornithine, citrulline, arginine, lysine, serine, threonine or tyrosine. Non-protein-like biologically active substances, such as, for instance, polysaccharides, nucleic acids, ampicillin or tyramine, can only be bound if they contain at least one primary amino or hydroxyl group. The active monomer units are sensitive to hydrolysis and, if they do not react with the active substances offered, can pass, in the presence of water, into hydrophilic carboxyl or hydroxyl groups. The activated groups are therefore present in the carrier material in generally greater number than is necessary for the bonding of the enzyme protein.

The carrier substances swell to several times their original volume in the aqueous enzyme solution. In this connection not only water but also the biologically active substance dissolved therein diffuses into the inside of the particles and is covalently bonded there. The swellability of the polymer beads is based on their content of hydrophilic groups. Monomer units with hydrophilic groups form an essential part of the polymer. They are derived from water-soluble, neutral, salt-like, acid or basic monomers. Monomers which give at least 10% aqueous solutions at room temperature are considered water-soluble within the meaning of the invention. Among the neutral monomers of this type, those having an amide group are of particular importance, particularly acrylamide, methacrylamide and N-vinyl pyrrolidone. Monomers which contain hydroxyl groups, i.e. ethylene glycol monoacrylate or monomethacrylate, are somewhat less hydrophilic. Monomers having salt-like groups are extremely hydrophilic and can participate in relatively small quantities in the structure of the copolymers of the invention. Monomers of this type are, for instance, vinyl sulfonic acid and its salts and the quaternized aminoalkyl esters of $\alpha,\beta$- unsaturated carboxylic acids, for instance methacryloxy ethyl trimethyl ammonium chloride. Monomers having carboxyl groups form salts in alkaline media and monomers having secondary or tertiary amino groups form salts in acid aqueous media, but these monomers and the monomer units resulting therefrom are hydrophilic even if they are not present in the form of their salts. Other water-soluble comonomers include acrylic and methacrylic acids, dialkylaminoethyl acrylates and methacrylates with 1 to 4 carbon atoms in the alkyl radicals and sulfoethylacrylates and methacrylates, as well as the salts thereof. Because of their tendency to react with epoxy groups, acid monomers such as vinyl sulfonic acid and its salts, monomers with carboxyl groups and their salts, and the sulfoethylacrylates and methacrylates and their salts are preferably not present in copolymers wherein comonomer A is a glycidyl compound.

The swellability of the carrier substances by water is not dependent solely on the hydrophilic groups in comonomer C, but is also based on the activated groups of comonomer A and on the free carboxyl or hydroxyl groups resulting therefrom by hydrolysis. A portion of up to 50 mol percent of the comonomers can be water-insoluble and of a less hydrophilic nature. Certain proportions of hydrophobic building blocks may be desirable for optimum effectiveness of the bound, biologically active substances. Water-insoluble monomers that are suitable include, for instance, acrylic and methacrylic acid esters of alkanols having 1 to 3 carbon atoms, nitriles of said acids, vinylidene chloride and the like. However, there are limits to the incorporation of such monomers because of the polymerization process. The process does not permit the use of monomers, such as, for example, acrylates and methacrylates of alcohols having four or more carbon atoms which, during the bead polymerization, dissolve preferentially in the continuous phase consisting, for instance, of higher aliphatic hydrocarbons.

A sufficient hydrophilicity of the copolymer is in any event present if a corresponding copolymer produced without the simultaneous use of cross-linking monomers would — at least after the hydrolysis of the activating groups — be soluble in water. By cross-linking, with comonomer B, which contains two or more radical-polymerizable $\alpha,\beta$-carbon double bonds, such as, for instance, mono- and polyethylene glycol dimethacrylates and diacrylates (the polyethylene glycol residue containing up to six ethylene groups), divinyl benzene, triallyl cyanurate, methylene-bis-acrylamide and -bis-methacrylamide and the like, the solubility in water is eliminated. The optimum degree of cross-linking, i.e. the selection of the quantity of cross-linking agent within the limits of 0.2 to 5 mol percent, is best determined empirically. The degree of cross-linking is to be considered sufficient when the polymer particles swell in water to 5 to 100 times in volume (bulk volume) or more, but retain their individual, approximately spherical shape even when they settle to form a layer in an aqueous medium. Free spaces, which are filled only with the aqueous phase, should remain between the particles. With insufficient cross-linking, the particles would be deformed upon settling and would not leave any intermediate spaces, while with too strong a cross-linking, only a slight swelling, if any, for instance to less than double the initial volume, would occur. A particularly wide-meshed cross-linking can be obtained by causing the polymerization, which will be described in detail below, to take place in the presence of a non-aqueous swelling agent.

Due to the sensitivity of the activated groups to hydrolysis, the polymerization is carried out in a medium which is as free of water as possible. With a water content of, for instance, one percent in the monomer phase, no substantial hydrolysis of the activated group occurs, but the water content must remain below the limit at which a considerable proportion of the reactive groups required for the enzyme bonding is hydrolyzed. This limit may differ depending on the sensitivity of the reactive group to water; as a rule it is between 2 and 5 mol percent, but in principle, operation under anhydrous conditions, i.e. with the complete absence of water, is preferred.

The development of cross-linked spherical particles of the carrier material of narrow particle-size distribution is obtained by a special process of bead polymerization in which a strongly non-polar liquid organic medium, which is not a good solvent for the monomers to be polymerized, is used as the continuous phase. Liquid aliphatic hydrocarbons, particularly those having at least seven carbon atoms in the molecule, are particularly suitable as such.

A clear difference in polarity between the monomer phase and the continuous phase is a prerequisite for any separation of phases at all taking place and for the monomer mixture to be present in the form of discrete droplets at the start of the polymerization. Only under this condition are spherical polymer particles of uniform size produced. The less polar the participating monomers are, the greater is their tendency to dissolve at least in part in the non-polar medium. This tendency can be counteracted by diluting the monomer phase with good solvents for the monomers which are immiscible with the non-polar organic medium, for instance formamide, dimethyl formamide trimethyl phosphate, hexamethyl phosphoric acid triamide, acetonitrile or dimethyl sulfoxide, in quantities of, for instance, 20 to 200 wt.%, referring to the amount of monomer. This measure at the same time promotes widemesh crosslinking and good swellability of the polymers. Limited solubility of the monomers in the continuous organic phase is not disturbing if the polymerization of this part of the monomers in the continuous phase is discouraged. In this case, namely to the extent that the monomers are converted into droplets by polymerization, rediffusion of the dissolved monomers into the droplets can occur. Therefore, polymerization initiators which dissolve as little as possible in the organic medium are preferably employed.

The monomer mixture is divided into small droplets in the organic medium by strong agitation. In order to maintain the condition of distribution produced by agitation on the part of the monomer phase -- which possibly contains solvent -- for the entire course of the polymerization, a dispersing agent which is soluble in the non-polar organic phase is preferably used. For this purpose, random copolymers or block or graft copolymers which are constructed of components of different polarity are particularly suitable. Random copolymers consisting of a predominant proportion, for instance 60 to 95 mol percent, of a non-polar monomer containing long-chain alkyl radicals, such as acrylic or methacrylic acid esters of alkyl alcohols having at least four carbon atoms in the alkyl radical, vinyl esters of fatty acids containing at least four carbon atoms, etc., and the balance consisting of polar, water-soluble monomers, such as methacryloyl choline chloride, dimethyl aminoethyl methacrylate, the salts of the latter with inorganic or organic acids, acrylic or methacrylic acid or acrylamide or methacrylamide have a good dispersing action. One can, however, also use graft or block copolymers produced by known methods (see copending patent application of Pennewiss et al., Ser. No. 116,648, filed Feb. 18, 1971, now U.S. Pat. No. 3,948,866 granted Apr. 6, 1976, incorporated herein by reference; see further German Offenlegungsschrift No, 20 09 218) in which monomers of the two mentioned types are not distributed at random, but in which they are polymerized separately from each other in different blocks of molecules or in the base chain and side chains of a graft polymer. The dispersing agents are able, even in amounts of 0.02 %, referred to the weight of the continuous phase, to maintain the state of suspension until the conclusion of the polymerization. The higher the quantity of dispersing agent selected and the more strongly agitation is effected, the smaller are the particles which are formed. A particle size of 0.1 to 1 mm in the unswollen state is desired.

The proportion of monomer phase — with or without addition of a solvent — to the continuous phase can be between 1 : 1 and 1 : 10, ratios of between 1 : 1.5 and 1 : 4 being preferred. The stability of the dispersion is greater the smaller the difference is between the densities of the two phases. By addition of halogenated hydrocarbons such as perchlorethylene, trichlorethylene, chloroform or carbon tetrachloride the density of the continuous phase can be adjusted to the density of the monomer phase, which latter is generally higher and increases during the course of the polymerization process.

The polymerization is initiated by a radical-forming initiator, for instance azo-bis-cyanovaleric acid or ammonium persulfate, which is readily soluble in the monomer phase and as difficulty soluble as possible in the continuous phase. With this initiator, the polymerization commences at temperatures of 50° to 80° C., However the solubility of the monomers in the continuous phase is undesirably high at these temperatures and precipitation polymerization may occur. It is therefore preferred to initiate the polymerization at lower temperature, for instance 15° to 30° C., by means of a redox initiator system. A benzoyl peroxide/dimethyl aniline system, for instance, is suitable. Other redox catalyst systems suitable for the polymerization process comprise dibenzoyl peroxide/N,N-dimethyl p-toluidine or N,N-bis-hydroxyethyl p-toluidine respectively, and tert. butyl permaleinate/S,S'-cadmium or zinc bis-(2-ethylhexyl thioglycolate). A polymerization inhibitor soluble in the continuous phase only, e.g. N-phenyl-N'-isopropylparaphenylene diamine, is preferably used to prevent precipitation polymerization. With good agitation and removal of heat, the polymerization can be concluded in one to three hours. The polymer beads are removed by filtration from the continuous phase and any adhering traces of the liquid phase are removed by washing with an anhydrous solvent. If the beads are produced in the presence of formamide, dimethyl formamide or dimethyl sulfoxide, these solvents are generally not removed from the beads which have been swollen therewith but are reacted with the aqueous enzyme solution in the moist condition in which they are obtained. It is even advantageous for the beads to be initially swollen prior to the reaction with such solvents when they are not used in the polymerization.

The reaction with the aqueous enzyme solution represents a competitive reaction between the desired covalent bonding of the biologically active substance and the undesired hydrolysis of the active groups. In this connection the desired bonding is favored by increasing the concentration of the biologically active substance in the aqueous solution. The solution should also be as free as possible of inactive accompanying proteins or other substances containing hydroxyl or amino groups which can otherwise also be bound to the carrier material. If a given pH range need not be maintained in order to maintain the activity, the reaction with the biologically active substances may take place at a pH of 5 to 8, and preferably at temperatures of 0° to 30° C. The reaction commences as the polymer beads become swollen with water. After a reaction time of from a few hours to a few days with slight agitation, the greatest part of the enzyme is bound and the excess active groups are hydrolyzed.

By far the greatest part of the biologically active substances are bound in the wide-mesh "hollow spaces" within the swollen particles. There the sensitive substances are protected against degradation by shearing forces which can occur upon agitation or with high velocity of flow in column reactors, but they are readily accessible to substrate molecules. Extremely high-molecular weight substrates will obviously be initially attacked predominantly by the active material bound on the polymer surface but can, with decreasing molecular size, increasingly enter into reaction with the active substances bound on the inside. The protected arrangement of the enzyme or other active molecules might also be the cause for the greater maintaining of their activity upon bonding to the polymer as compared with carrier substances of other structure. The latter are generally activated as solid particles and bind the enzyme or other active material predominantly on the surface, where it can easily be damaged by shearing forces. Upon the bonding of active substances to non-crosslinked copolymers of maleic anhydride with simultaneous crosslinking, the active molecules are presumably bound also in the interior of the carrier particles but are so securely enclosed by subsequent crosslinking that reaction with substrate molecules is no longer possible.

Among the biologically active substances which can be bound to the bead-shaped carriers of the invention, the enzymes, and particularly the hydrolases, are of particular importance. As examples of suitable enzymes, mention may be made of proteases such as fungus and bacterial proteases, trypsin, chymotrypsin, pancreatin, as well as amylases, ribonucleases, desoxyribonucleases, etc. The high activity of the bound materials with respect to high-molecular weight substrates is particularly advantageous.

Conversely by means of bound enzyme substrates or inhibitors, enzymes dissolved in aqueous media or contained in biological material can be selectively removed therefrom or made inactive. The enzymes absorbed can be removed from the carrier-bound substrates by changing the pH or the electrolyte content of the unbound medium, the enzymes being in this way isolated in pure form. There are numerous further possibilities of affecting the behavior of biological systems by means of carrier-bound hormones, such as insulin or hypertensin, or antibiotics such as ampicillin, or antibodies, antigens, biogenic amines and various peptides. Mixtures of different biologically active substances may also be bound simultaneously. Biologically active substances which would mutually impair each other's effect in free condition can be separately bound on different portions of the carrier substances of the invention, the resultant products mixed and the mixture used.

The carriers reacted with biologically active substances contain in typical cases 5 to 50, and preferably 10 to 30% by weight of bound material, referred to the dry weight of carrier and biological material. The products are present in water as gel-like spherical particles of a diameter of generally 1 to 5 mm. As a result of their strong swelling, they have a density which differs only slightly from the aqueous medium, so that they can be maintained in suspension even by only slight stirring. When used as column or reactor packing, the velocity of flow of the substrate solution is limited only by the speed of diffusion of the substrate.

The loss in activity of the bound biologically active material upon use and storage is clearly less than upon the storage of the non-bound substances under the same conditions. Therefore, by frequent reuse for batchwise treatment or by long life in case of continuous use, a substantially higher utilization of the biological activity is possible than when using the unbound substances.

As an example of the advantageous processes which are made possible by means of carrier-bound enzymes, the isolation of nucleic acids from biological material deserves mention. Proteins in particular occur as byproducts in such material and are difficult to remove. Heretofore they had to be removed by expensive extraction processes with phenol. They can, to be sure, also be degraded with soluble proteolytic enzymes, but these enzymes are themselves proteins which also can be removed only by extraction with phenol. However, the proteins can be easily and completely degraded by means of a carrier-bonded protease. After the carrier-bonded enzyme has been removed by filtration, the substrate solution no longer contains any high-molecular weight components in addition to the nucleic acids. The nucleic acids themselves are frequently separated further by known methods into ribonucleic acid and desoxyribonucleic acid. In this connection also the complete removal of the other component always caused a considerable expenditure of time. By means of carrier-bonded ribonucleases, traces of ribonucleic acid can now be removed from the desoxyribonucleic acid fraction. Conversely, ribonucleic acid can be obtained free of desoxyribonucleic acid by treating it with carrier-bonded desoxyribonuclease.

Manufacture of Bead-Shaped Carrier Polymers

EXAMPLE 1

167 g of n-heptane and 333 g of perchloroethylene which has been dried over molecular sieve 4 A were placed in a round-bottom flask (500 ml). 2 g of benzoyl peroxide and 0.02 g of a stabilizer (tradename Bayer 4010 Na) were dissolved therein. At 20° C., a monomer solution was added consisting of:
  80 g dimethyl formamide,
  60 g acrylamide,
  60 g methacrylic anhydride,
  1.5 g ethylene glycol dimethacrylate, and
  0.1 g emulsifier (random copolymer of n-butyl methacrylate an methacryloyl choline chloride = 90/10).

All monomers and solvents were free of water and furthermore both the receiver and the monomer solution were freed of oxygen by means of dry $CO_2$. (This is true also in the following examples).

The monomer phase was distributed in the organic phase by constant agitation. The starting of the reaction was effected by addition of the second redox partner (1 g of dimethyl aniline). With a relatively short time of polymerization (30 min.), the temperature was maintained substantially constant at 20° C. – 25° C. by cooling with a coolant mixture. The resultant beads were freed from the organic phase by settling and short suction filtering. They were furthermore swollen slightly with dimethyl formamide and used in this condition for reaction with an enzyme.

EXAMPLE 2

167 g of n-heptane and 333 g of perchloroethylene were placed in a round-botom flask (1000 ml). At 20° C., a monomer solution was added consisting of:
  80 g formamide,
  60 g methacrylate anhydride,
  60 g acrylic acid,
  0.8 g ethylene glycol dimethacrylate, and
  0.1 g emulsifier (same as Example 1).

The monomer phase was distributed in the organic phase by agitation. In order to initiate the reaction, 2 g of benzoyl peroxide and 1 g of dimethyl aniline were added one after the other. The polymerization, which started immediately, was maintained under control by cooling with a coolant mixture; an increase in temperature of more than 25° C. should be avoided.

The beads obtained were freed from the organic phase by settling and short suction filtration.

EXAMPLE 3

42 g of n-heptane, 84 g of perchloroethylene and 0.5 g of benzoyl peroxide were placed in a round-bottom flask (250 ml). At 20° C. the following solution was added:
  20 g dimethyl formamide,
  12 g acrylamide,
  3 g acrylic acid,
  15 g methacrylic anhydride,
  0.025 g emulsifier (as in Example 1), and
  0.57 g triethylene glycol dimethacrylate.

The monomer phase was distributed in the organic phase by agitation and freed from oxygen by the introduction of dry $CO_2$. The reaction was initiated by addition of 0.25 g of dimethyl aniline. The reaction was complete after about 2 hours with continuous external cooling of the batch. The beads obtained were removed.

EXAMPLE 4

60 g of n-heptane, 120 g of perchloroethylene and 0.25 g of benzoyl peroxide were placed in a round-bottom flask (250 ml). At 20° C. a solution was added consisting of:
  20 g dimethyl formamide,
  2 g acrylic acid,
  0.025 g emulsifier (as in Example 1),
  3 g acrylic anhydride,
  25 g acrylamide, and
  0.38 g ethylene glycol dimethacrylate.

The monomer phase was dispersed in the organic phase and degased by agitation. The reaction was initiated by addition of 0.12 g of dimethyl aniline. External cooling of the batch was necessary in order to maintain the temperature at 25° C. Beads were obtained.

EXAMPLE 5

165.5 g of perchloroethylene, 83.5 g of n-heptane and 0.5 g of benzoyl peroxide were placed in a round-bottom flask (500 ml). At 20° C. a monomer solution was added consisting of:
  20 g formamide,
  15 g acrylamide,
  15 g acrylic anhydride,
  0.025 g emulsifier (same as Example 1), and
  0.76 g ethylene glycol dimethacrylate.

The monomer solution was dispersed in the organic phase and degased with agitation. The reaction was initiated by the addition of 0.25 g of dimethyl aniline. The reaction was very vigorous. The batch was cooled externally with a coolant mixture. Beads were obtained.

EXAMPLE 6

122 g of n-heptane, 77 g of perchloroethylene and 0.14 g emulsifier (random copolymer of n-butylmethacrylate/methacryloyl choline chloride 95:5, molecular weight = 20,000) were placed in a round-bottom flask (500 ml). At 20° C. a monomer solution was added consisting of
  25 g formamide,
  0.5 g dibenzoyl-peroxide,
  10.6 g acrylamide,
  5.2 g methacrylic anhydride,
  5.2 g methacrylate, and
  0.2 g N,N'-methylene-bis(methacrylamide).

The monomers and solvents used were free of water. Both the receiver and the monomer solution were freed from oxygen by replacing air with nitrogen. Polymerization was initiated by adding 0.35 g dimethyl aniline. After 30 minutes the temperature rose, and was maintained at 25° – 30° C. by external cooling. After 4 hours stirring the beads were separated from the organic phase by settling and short suction filtration. They were washed with acetone and dried in vacuum (10 torr) at 40° C.

Instead of formamide the following solvents can be used: dimethyl formamide, dimethyl sulfoxide, acetonitrile, trimethyl phosphate, and hexamethyl phosphoric acid triamide.

EXAMPLE 7

42 g of n-heptane, 84 g of perchloroethylene and 0.5 g of benzoyl peroxide were placed in a round-bottom flask (250 ml). The following solution was added at 20° C.:
  20 g dimethyl formamide,
  5 g formamide,
  15 g methacrylic anhydride,
  7.5 g acrylamide,
  7.5 g methacrylamide,
  0.57 g triethylene glycol dimethacrylate, and
  0.025 g emulsifier (same as Example 1).

The monomer phase was dispersed in the organic phase and degased with agitation. The reaction was initiated by the addition of 0.25 g of dimethyl aniline. The polymerization proceeded with only a slight development of heat so that only slight external cooling was sufficient. Fine beads were obtained.

EXAMPLE 8

87 g of n-heptane, 55 g of perchloroethylene and 0.1 g of the emulsifier of Example 6 were placed in a round-bottom flask (500 ml). After cooling to 20° C., the following solution was added:
17.5 g formamide,
13.5 g acrylamide,
1.5 g acryloyl N-hydroxy succinimide, and
0.375 g ethylene glycol dimethacrylate.

The monomer phase was dispersed in the organic phase and degased with agitation. The reaction was initiated by addition of 0.25 g of dimethyl aniline. Fine beads were obtained.

EXAMPLE 9

87 g of n-heptane, 55 g of perchloroethylene and 0.1 g of the emulsifier of Example 6 were placed in a round-bottom flask (500 ml). After cooling to 20° C., the following solution was added:
17.5 g formamide,
12 g acrylamide,
3 g glycidylacrylate, and
0.375 g ethylene glycol dimethacrylate.

The monomer phase was dispersed in the organic phase and degased with agitation. The reaction was initiated by the addition of 0.5 g of dimethyl aniline in two portions. Fine beads were obtained.

REACTION OF THE BEAD POLYMERS WITH BIOLOGICALLY ACTIVE SUBSTANCES

EXAMPLE 10

3 g of the bead polymer produced in Example 1 were swollen for 5 hours at 90° C. with anhydrous dimethyl formamide. Thereupon a solution of 1 g of trypsin in 100 ml of 0.2 M phosphate buffer (pH 7.5) was added with vigorous agitation and cooling by ice, the agitation was continued for 6 hours, and the batch was set aside overnight at 5° C.

The product was washed five times with sodium chloride solution, in which the beads were stirred for about 30 minutes in water; solid sodium chloride was added up to a concentration of 6%, stirring was continued for an additional 30 minutes and filtration was effected. Finally the beads were washed twice with, in each instance, 2 liters of 0.05 M phosphate buffer (pH 7.5, 0.01% sodium azide) and suction-filtered. Moist yield: 85 g. Enzyme content (determined by ultraviolet spectrometry after dissolving the beads in 0.5 N NaOH at 100° C.): 22.8%, referred to dry weight.

Catalytic activity: Within 60 minutes, 100 mg of the trypsin beads (dry weight) split 220$\mu$ mol peptide bonds on casein. This corresponds to the degradation power of 5 mg of dissolved crystalline trypsin under the same test conditions (substrate concentration 3.3%, 37° C., automatic titration of the liberated carboxyl groups with 0.1 N NaOH at a pH of 8.1). The catalytic activity of the trypsin beads with respect to high-molecular substrate is about 20%, referred to the trypsin content thereof. After five repeated uses, no decrease in activity was observed.

Upon use of the bead polymer produced in Example 8 as carrier substance, substantially the same result was obtained.

EXAMPLE 11

Chymotrypsin beads were prepared in the same manner as in Example 10. Enzyme content: 26%. Catalytic activity with respect to high-molecular substrate (casein): in 60 min. 100 mg beads (dry weight) split 250$\mu$ mol peptide bonds under standard conditions; this corresponds to 25% of the activity of non-bound trypsin.

EXAMPLE 12

Pancreatin, a dry powder obtained from pancreas glands, which is rich in proteolytic enzymes was reacted in the manner described in Example 10 with a series of bead polymers in a weight ratio of 1:1. The proteolytic splitting power of the carrier-bonded enzymes obtained (in each case 100 mg dry beads) with respect to a 3.3% casein solution within 60 min. under standard conditions is shown in the following table.

| Bead polymer used for the preparation of the carrier-bound enzyme | $\mu$mol split peptide bond per 100 mg, 60 min. |
| --- | --- |
| Product of Example 1 | 250 |
| Product of Example 2 | 300 |
| Product of Example 4 | 350 |
| Product of Example 5 | 800 |

EXAMPLE 13

Protease from Streptomyces griseus (Pronase E, manufactured by E. Merck AG) was reacted in a weight ratio of 1:2 in the manner indicated in Example 10 with the bead polymer prepared in accordance with Example 1. From 5 g of bead polymer and 2.5 g of enzyme, 142 g of moist beads were obtained.

Protein content: 5.2% (protein determination with Folin-Ciocalteu reagent after dissolving the beads in 0.5 N NaOH).

Catalytic activity with respect to high-molecular weight substrate (casein, standard conditions): 100 mg Pronase beads (dry weight) split 399$\mu$ mol peptide bonds per 60 minutes. After five uses, no loss in activity was observed. Activity with respect to high-molecular weight substrate (casein): 15%, referred to free enzyme. The product is inactive with respect to DNA (for instance from trout sperm).

EXAMPLE 14

Obtaining of High-Molecular Nucleic Acids from Liver by Removal of the Protein with Pronase Beads 13.4 g of mouse liver were homogenized in 60 ml of 0.05 M phosphate buffer (pH 8, 0.02 M EDTA, 2% Sarkosyl-NL 97 manufactured by Geigy AG) in a mortar cooled with dry ice and then stirred for 24 hours with Pronase beads in accordance with Example 13 (40 g moist beads). The proteolysis was noted by automatic titration with 0.1 N NaOH. A total of 24 ml of NaOH was consumed. Thereupon suction filtration was effected over a glass frit, followed by centrifuging. The centrifuge residue was removed and precipitated in the cold with an equal volume of ice-cold isopropyl alcohol. The precipitated, thread-like product was washed several times with aqueous solution and then finally with pure isopropyl alcohol and then finally with ether and dried on filter paper in a vacuum (160 mg dry yield).

The DNA content of the dry product was determined by Kissane's fluorimetric method, the RNA content by Webb's method and the protein by the Folin method:

| | |
|---|---|
| DNA | 18% |
| RNA | 32% |
| Protein | 0.2% |
| $H_2O$ | 20% |

The results show that with Pronase beads, DNA can be strongly concentrated from homogenized liver. The yield is practically quantitative.

For further purification, 120 mg of the dry product were dissolved in buffer and degraded by treatment with soluble ribonuclease and α-(1,4)-amylase glycogen and RNA. Thereupon the added enzymes were degraded by shaking with Pronase beads and 20 mg dry product was obtained by precipitation of isopropyl alcohol after corresponding washing and drying. the product, aside from 18% water, still contained only DNA.

EXAMPLE 15

250 mg of ribonuclease A (manufactured by the Serva Co., chrom. uniform, free of DNase, RNase-B and proteases) were dissolved in 30 ml of 0.2 M phosphate buffer (pH 7.5) and reacted in the manner described in Example 10 with 1000 mg of the bead polymers produced in Example 1.

Yield: 27.7 g moist beads.

Protein content: 11% (referred to dry weight).

Catalytic activity with respect to high-molecular weight substrate: 2 g moist beads (corresponding to 84 mg dry beads), 8 ml of 0.05 M phosphate buffer of a pH of 7.5 and 20 ml of substrate (4% yeast-RNA manufactured by the firm of Boehringer, Mannheim, adjusted by means of NaOH to a pH of 8) were incubated at 37° C.

Under the test conditions, 100 mg of beads (dry weight) split 640 μ mol of phosphoric ester bonds in 60 minutes. Compared with non-bonded soluble RNase, the activity of the RNase beads, referred to their protein content with respect to high-molecular substrate, is 55%.

EXAMPLE 16

44 mg of desoxyribonuclease I (manufactured by Serva Co., lyophyl.pure, from ox pancreas) were dissolved in 8 ml of 0.2 M phosphate buffer (pH 7.5) and reacted with 200 mg of the methacrylic anhydride-methacrylamide beads prepared in Example 1 in the manner described for trypsin in Example 10.

Yield: 5.4 g moist beads.

Protein content: 4.5% (referred to dry weight).

The product is active with respect to DNA from trout sperm with a molecular weight of 18 million.

EXAMPLE 17

500 mg of insulin were dissolved in 50 ml of 0.2 M phosphate buffer (pH 7.5, 2 mg EDTA/ml) and stirred for 10 hours at 5° C. with 500 mg of acrylic anhydride-acrylamide beads prepared in accordance with Example 4 which had been pre-swollen in dimethyl formamide, and then washed ten times by the water-sodium chloride solution method (see Example 10).

Protein content of the beads: 28%.

Glucagon and hypertensin beads were prepared in the same manner.

EXAMPLE 18

Trypsin inhibitor from pancrease was reacted for 30 hours with a bead polymer in accordance with Example 9 at a pH of 9.5 (aqueous bicarbonate buffer) and then washed five times with the water-sodium chloride solution method, and furthermore alternately three times with 1% acetic acid and 0.2 M phosphate buffer, pH 7.5. Protein content of the trypsin-inhibitor beads: 8.5% (referred to dry weight).

Trypsin can be bonded specifically to the inhibitor beads and can be desorbed in the acid pH range without loss of activity.

EXAMPLE 19

500 mg of tyramine were reacted for 12 hours in 25 ml of bicarbonate buffer (pH 9) with 1000 mg of the bead polymer prepared in Example 9 at room temperature. After removal of the non-bound tyramine by washing with 5% acetic acid, tyramine beads were obtained which contained 20% tyramine, referred to the dry weight. The tyramine content was determined by ultraviolet spectrometry after alkaline hydrolysis in 0.5 N NaOH at 100° C.

The antibiotic ampicillin was bound in similar manner to the same type of bead.

EXAMPLE 20

84 g of n-heptane, 166 g of perchloroethylene and 1 g emulsifier (block-copolymer n-butylmethacrylate/methacryloyl cholin chloride, see Example A of Patent Application Ser. No. 116,648) were placed in a round-bottom flask (500 ml). At 20° C. a monomer solution was added consisting of 31 g formamide,
18 g acrylamide,
18 g methacrylic anhydride,
18 g methacryloyl cholin chloride,
3 g 2-dimethylamino ethyl methacrylate, and
3 g allyl-methacrylate.

The monomer solution was dispersed in the organic phase and degassed with agitation. Polymerization was initiated by addition of 1 g dibenzoyl peroxide and 0.5 g dimethyl aniline. External cooling of the batch was necessary in order to maintain the temperature at 25° C. After agitating for 8 hours, an equal volume of acetone was added. The beads shrank and became hard, thus avoiding sticking together. They were separated from the organic phase by settling and suction filtration. Then they were washed with dry acetone and dried in vacuum (10 mm Hg) at 40° C.

EXAMPLE 21

125 g of n-heptane, 125 g of perchlorethylene and 1 g emulsifier (block copolymer n-butyl methacrylate/sodium methacrylate 90/10, manufactured analogous to Example A of Patent Application Serial No. 116,648) were placed in a round-bottom flask (500 ml). At 20° C. a monomer solution was added consisting of 31 g formamide,
18 g acrylamide,
18 g methacrylic anhydride,
18 g sulfoethyl methacrylate,
6 g acrylic acid,
0.2 g tetraethyleneglycol-dimethacrylate.

Polymerization and working up were performed as in Example 20.

EXAMPLE 22

174 g of n-heptane, 110 g of perchlorethylene and 0.2 g emulsifier (same as Example 6) were placed in a round-bottom flask (500 ml). At 20° C. a monomer solution was added consisting of
- 70 g formamide
- 6 g acrylamide
- 6 g N-vinyl-pyrrolidone
- 3 g glycidyl-acrylate
- 0.1 g N,N'-methylene-bis(methacrylamide)
- 0.5 g dibenzoyl peroxide.

Polymerization was initiated by addition of 0.5 g dimethyl aniline. Working up was performed as in Example 20.

EXAMPLE 23

225 g of mineral oil (3.9 cSt/100° C.), 0.75 g emulsifier (same as Example 6), and 0.02 g of a stabilizing agent (tradename "Aelterungsschutzmittel 4010 An", Bayer) were placed in a round-bottom flask (500 ml) and heated to 70° C. The following monomer mixture was added drop by drop within one hour:
- 40 g dimethyl formamide,
- 40 g methacrylic anhydride,
- 20 g 2-hydroxy-ethyl-methacrylate,
- 0.5 g 4,4-azo-bis-(4-cyanovaleric acid), and
- 1.5 g ethylene glycol dimethacrylate.

Agitation was continued for 3 hours at 70° C. The oil phase was removed by decantation from the resultant beads. They were washed with acetone and dried.

EXAMPLE 24

Beads (1 g), as obtained in Example 1, were swollen in dimethylformamide (DMFA) at 95° C. for 5 hours. After cooling to room temperature, the excess of DMFA was poured off. Then, 2.5 g maltose (monohydrate, A grade, dissolved in 12 ml DMFA) was added, and the mixture was stirred at 90° C. for 20 hours. Phosphate buffer (300 ml, 0.2 M, pH 7.5) was added, and after standing overnight, the product was washed, as described in Example 10.

An aliquot of the final product was washed ten times with water, dehydrated with acetone and carefully dried to constant weight at 60° C. in vacuo. Determination of the oxygen and nitrogen content of the product was carried out, and from the O/N ratio a maltose content of approximately 35% was calculated.

EXAMPLE 25

87 g of n-heptane, 55 g of perchloroethylene, 0.5 g of dibenzoyl peroxide, 0.1 g of a statistical copolymer of 95 parts by weight of n-butylmethacrylate, and 5 parts by weight of methacryloxyethyl-dimethylammonium-chloride as an emulsifying agent were put into a 500 ml round-bottom flask. After cooling to 20° C., the following solution was added:
- 17.5 g formamide,
- 12 g of acrylamide,
- 3 g of glycidyl acrylate,
- 0.375 g of ethylene glycol dimethacrylate.

The monomer phase was dispersed in the organic phase by stirring and degassed. The polymerization was initiated by the addition of 0.5 g of dimethyl aniline. Fine pearls were produced.

EXAMPLE 26

The technique of Example 25 was repeated but, instead of ethylene glycol dimethacrylate, the same amount of N,N'-methylene-bis-methacrylamide was used.

EXAMPLES 27 – 33

The technique of Example 26 was repeated but instead of glycidyl acrylate, the following compounds were employed in the same amount:
- Example 27, glycidylmethacrylate
- Example 28, 4,5-epoxy-pentylacrylate
- Example 29, 4-(2,3-epoxypropyl)-cyclohexylmethacrylate
- Example 30, allyl glycidyl ether
- Example 31, ethylene glycol — monoglycidyl ether — acrylate
- Example 32, 9,10-epoxystearylacrylate
- Example 33, 4-(2,3-epoxypropyl)-n-butylmethacrylate.

In each case, fine pearls were obtained.

EXAMPLES 34 and 35

A pearl polymer was prepared as in Example 26 with the difference that, instead of 12 g of acrylamide and 3 g of glycidyl acrylate, the following were introduced:
Example 34:
- 9 g of acrylamide
- 3 g of methyl acrylate
- 3 g of glycidyl acrylate Example 35:
- 9 g of acrylamide
- 6 g of glycidyl acrylate

EXAMPLE 36

42 g of n-heptane, 84 g of perchloroethylene, and 0.5 g of benzoyl peroxide were placed into a round-bottom flask. The following monomer solution was added at 20° C.:
- 20 g of dimethylformamide,
- 5 g of formamide,
- 5 g of glycidyl methacrylate,
- 12.5 g of acrylamide,
- 12.5 g of methacrylamide,
- 0.57 g of triethylene glycol-dimethacrylate,
- 0.025 g of the emulsifying agent of Example 25.

The monomer solution was dispersed into droplets by stirring. Polymerization was initiated by the addition of 0.25 g of dimethyl aniline. It proceeded with the weak release of heat with gentle exterior cooling. Fine pearls are obtained.

EXAMPLE 37

84 g of n-heptane, 166 g of perchloroethylene, and 1 g of an emulsifier (a block copolymer of n-butylmethacrylate and methacryloyl-choline-chloride — cf. Example A of U.S. patent application Ser. No. 116,648 of Feb. 18, 1971) were placed in a round-bottom flask. At 20° C., the following monomer solution was introduced and dispersed into fine droplets by stirring:
- 31 g of formamide,
- 27 g of acrylamide,
- 9 g of glycidyl acrylate,
- 18 g of methacryloyl-choline-chloride,
- 3 g of 2-dimethylaminoethyl-methacrylate, and
- 3 g of allylmethacrylate.

Polymerization was started by the introduction of 1 g of dibenzoyl peroxide and 0.5 g of dimethyl aniline. By exterior cooling the temperature was kept at 25° C. After 8 hours the batch was combined with an equal volume of acetone. The pearls shrivel and become hard so that they are no longer sticky. They are permitted to settle and then separated from the liquid phase on a suction filter. They are washed again with acetone and dried in vacuum at 10 mm Hg.

EXAMPLE 38

225 g of mineral oil (viscosity = 3.9 centistokes/100° C.) and 0.75 g of the emulsifier employed in Example 25 are placed in a round bottom flask and heated to 70° C. Then, within an hour, the following monomer solution is added dropwise:
- 40 g of dimethyl formamide,
- 15 g of glycidyl methacrylate,
- 45 g of 2-hydroxyethyl-methacrylate,
- 0.4 g of 4,4-azo-bis-(4-cyanovalerianic acid), and
- 2.5 g of tetraethylene glycol-dimethacrylate.

After stirring for three hours at 70° C., polymerization is concluded. The oil phase is decanted after the pearls have settled and the latter are washed with acetone.

EXAMPLE 39

100 mg of ribonuclease-A (RNase) were dissolved in 18 ml of 0.2 M phosphate buffer (Na$_2$HPO$_4$, pH = 9) and then shaken vigorously for about 30 minutes with 2000 mg of the pearl polymer of Example 26, whereby the enzyme solution was completely absorbed by the pearls. The product was left to stand for 24 hours at room temperature. After washing four times in 1 M aqueous sodium chloride and washing twice with 0.05 M phosphate buffer, 16.4 g of moist pearls were obtained after suction filtration through a glass frit.

The coupling yield of RNase amounted to 73 percent, as determined by acid hydrolysis and amino acid analysis in an amino acid analyzer (Beckmann, Unichrome C) according to the method of Stein and Moore [Analyt. Chem. 30, 1185, 1190 (1958)]. The enzymatic activity was determined with RNA (from yeast) as the substrate at 37° C. and a pH of 7.5 and was 45 percent compared with the free enzyme. The activity of the pearls was not decreased even after a 20-fold substrate decomposition.

EXAMPLE 40

The procedure of Example 39 was repeated with the difference that the enzyme trypsin was employed instead of RNase. Coupling yield: 83 percent.

The enzymatic activity against casein as the substrate at 37° C. and at a pH of 8 was 33 percent of the free enzyme. After a 40-fold repeated use (casein decomposition), the activity was still 90 percent of the initial activity. The loss of 10 percent can be explained as a loss in enzyme during filtration.

EXAMPLE 41

The procedure of Example 40 was repeated using the enzyme chymotrypsin instead of trypsin.
Coupling yield: 68 percent.
Enzymatic activity (casein as the substrate, pH = 8, 37° C): 39 percent of the free enzyme.

EXAMPLE 42

10 g of pearls according to Example 35 were reacted with glucamylase (amyloglucosidase, 150 AG/me) in the same way as in the preceding Examples with the difference that a pH of 9 was established in the reaction mixture with sodium hydroxide.

Activity yield in the product: 29 percent.

2 g of pearls and 20 ml of dextrine solution (30 percent, in water) were shaken overnight at room temperature and then a small amount of the solution was chromatographed on "Biogel P 2" according to the method of Dellwey et al. [Monatszeitschrift fur Brauerei 22, 177 (1969)]. A complete decomposition of the substrate to glucose was determined. The glucamylase pearls were used repeatedly 100 times for the decomposition of dextrine, whereby a complete conversion of the substrate to glucose was always observed.

EXAMPLES 43 - 49

The technique of Example 39 was repeated using, however, the following pearl polymers:

| Example | Pearl Polymer According to Example | Coupling Yield | Enzyme Activity |
|---|---|---|---|
| 43 | 27 | 63 | 42 |
| 44 | 28 | 64 | 47 |
| 45 | 29 | 52 | 46 |
| 46 | 30 | 32 | 37 |
| 47 | 31 | 81 | 58 |
| 48 | 32 | 70 | 49 |
| 49 | 33 | 53 | 34 |

EXAMPLE 50

The technique of Example 39 was employed with the difference that insulin was used instead of ribonuclease.
Coupling yield: 87 percent.

EXAMPLE 51

Pearls according to Example 31 were reacted with concanavalin-A (con-A) according to the technique of Example 39.
Yield of bound con-A: 89 percent.

Example 52

1000 mg of pearls according to Example 31 were reacted with 200 mg of ampicillin-sodium salt in 5 ml of dimethylformamide for 24 hours at 30° C.
Coupling yield: 93 percent.

What is claimed is:
1. A water-swellable, cross-linked bead copolymer prepared by the method comprising:
   a. dissolving a monomer mixture consisting essentially of
      1. an ethylenically-unsaturated radical-polymerizable comonomer having a glycidyl group,
      2. a cross-linking comonomer having at least two radical-polymerizable α, β-carbon double bonds, but otherwise free of the functional groups found in monomer (1),
      3. a radical-polymerizable water-soluble mono-unsaturated comonomer, comonomers (1), (2), and (3) constituting from about 50 to 100 mol percent of the monomer mixture with the balance, if any, being
      4. a water-insoluble radical-polymerizable mono-unsaturated compound, comonomer (1) comprising at least 2 mol percent, comonomer (2) comprising 0.2 to 5 mol percent, and comonomer (3) comprising at least 10 mol percent of the monomer mixture, in from 20 to 200 percent, by weight of the monomer mixture, of a non-aqueous solvent for said monomer mixture;

b. combining the solution with a free radical-forming initiator soluble in said solution;

c. suspending the resulting solution, in the form of droplets, in a continuous phase of a non-polar organic liquid which is immiscible with said non-aqueous solvent and is not a solvent for said monomer or said initiator;

d. polymerizing said monomer mixture at a temperature at which said initiator forms free radicals, whereby said bead copolymer is formed; and e. separating said bead copolymer from said continuous phase of organic liquid.

2. A copolymer as claimed in claim 1 which is washed with an anhydrous solvent after separation from said continuous phase of organic liquid.

3. A copolymer as claimed in claim 2 which is washed with acetone after separation from said continuous phase of organic liquid.

4. A copolymer as in claim 1 wherein comonomer (1) is an ester or ether formed between a glycidyl alcohol and an unsaturated carboxylic acid or an unsaturated alcohol, respectively.

5. A copolymer as in claim 1 wherein comonomer (1) is allyl glycidyl ether or an acrylate or methacrylate ester of an aliphatic or cycloaliphatic glycidyl alcohol or glycidyl ether alcohol having 3 to 18 carbon atoms.

6. A copolymer as in claim 1, wherein comonomer (2) is a mono- or lower polyethylene glycol dimethacrylate or diacrylate, divinyl benzene, triallyl cyanurate, methylene-bisacrylamide or methacrylamide, or a combination thereof.

7. A copolymer as in claim 6, wherein comonomer (2) is ethylene- or triethylene glycol dimethacrylate.

8. A copolymer as in claim 1, wherein comonomer (3) is a vinyl or vinylidene compound containing an amido, hydroxyl, carboxyl, tertiary amino, quaternary ammonium or sulfonic acid group.

9. A copolymer as in claim 8, wherein comonomer (3) is a vinyl or vinylidene compound containing an amido group.

10. A copolymer as in claim 1, wherein comonomer (3) is acryl- or methacrylamide, vinyl pyrrolidone, ethylene glycol- or propylene glycol monoacrylate or monomethacrylate, acrylic- or methacrylic acid, dialkylaminoethyl acrylate or methacrylate with 1 to 4 carbon atoms in the alkyl substituents, vinyl sulfonic acid, sulfoethyl acrylate or methacrylate, a salt thereof, or a combination thereof.

11. A copolymer as in claim 1, wherein the content of comonomer (3) is more than 20% by weight.

12. A copolymer as in claim 11, wherein the content of comonomer (3) is from 50 to 80% by weight.

* * * * *